(12) United States Patent
Cook et al.

(10) Patent No.: US 10,537,729 B2
(45) Date of Patent: Jan. 21, 2020

(54) TRIGEMINAL NEUROSTIMULATION BASED UPON PULSE COUNTING AND CHRONOBIOLOGY

(71) Applicant: NeuroSigma, Inc., Los Angeles, CA (US)

(72) Inventors: Ian A. Cook, Los Angeles, CA (US); Colin Kealey, Los Angeles, CA (US)

(73) Assignee: NEUROSIGMA, INC., Los Angeles, CA (US)

( * ) Notice: Subject to any disclaimer, the term of this patent is extended or adjusted under 35 U.S.C. 154(b) by 48 days.

(21) Appl. No.: 15/600,499

(22) Filed: May 19, 2017

(65) Prior Publication Data

US 2017/0252552 A1    Sep. 7, 2017

Related U.S. Application Data

(63) Continuation of application No. PCT/US2015/061680, filed on Nov. 19, 2015.

(60) Provisional application No. 62/081,650, filed on Nov. 19, 2014.

(51) Int. Cl.
| | |
|---|---|
| *A61B 5/00* | (2006.01) |
| *A61N 1/04* | (2006.01) |
| *A61N 1/36* | (2006.01) |
| *A61B 5/0482* | (2006.01) |

(52) U.S. Cl.
CPC .......... *A61N 1/0456* (2013.01); *A61B 5/0482* (2013.01); *A61B 5/4857* (2013.01); *A61N 1/0492* (2013.01); *A61N 1/36025* (2013.01); *A61N 1/36* (2013.01); *G01N 2800/28* (2013.01); *G01N 2800/30* (2013.01)

(58) Field of Classification Search
CPC .. A61B 5/0482; A61B 5/4857; A61N 1/0456; A61N 1/0492; A61N 1/36; A61N 1/36025; G01N 2800/28; G01N 2800/30
See application file for complete search history.

(56) References Cited

U.S. PATENT DOCUMENTS

| | | | |
|---|---|---|---|
| 2003/0202990 A1 | 10/2003 | Donovan et al. | |
| 2005/0149141 A1 | 7/2005 | Starkebaum | |
| 2009/0210028 A1* | 8/2009 | Rigaux | A61N 1/0456 607/46 |
| 2011/0106220 A1* | 5/2011 | DeGiorgio | A61N 1/0456 607/72 |

FOREIGN PATENT DOCUMENTS

WO    WO 2014/176450    10/2014

* cited by examiner

*Primary Examiner* — George Manuel
(74) *Attorney, Agent, or Firm* — Haynes and Boone LLP

(57) ABSTRACT

Trigeminal nerves are stimulated based upon pulse counting and chronobiology. A cutaneous electrode assembly is applied to the forehead to stimulate the ophthalmic nerves. A method may include determining a number of pulses to be administered to a patient based upon the disorder being treated, and pulsing current through an electrode assembly to stimulate the patient's supraorbital and supratrochlear nerves with the determined number of pulses. Another method may include determining a pulse repetition frequency for pulses to be administered to a patient based upon the disorder being treated, and pulsing current through an electrode assembly to stimulate the patient's supraorbital and supratrochlear nerves at the pulse repetition frequency.

20 Claims, 3 Drawing Sheets

TRIGEMINAL NEUROSTIMULATION BASED UPON PULSE COUNTING AND CHRONOBIOLOGY

CROSS-REFERENCES TO RELATED APPLICATIONS

This application is a continuation of International Application No. PCT/US2015/061680, filed Nov. 19, 2015, which claims the benefit of U.S. Provisional Application No. 62/081,650, filed Nov. 19, 2014, which are hereby incorporated by reference in their entirety.

TECHNICAL FIELD

The present disclosure relates to neurostimulation, and more specifically to the stimulation of cranial nerves to treat disorders.

BACKGROUND

Neurological disorders such as seizure disorders are usually treated with medication. However, there are patients who are not helped by medication—they may not be able to tolerate the side effects or the medication itself is not efficacious for their particular disorder. This is a significant problem in that seizure disorders can be life threatening. Moreover, the quality of life for victims of severe epilepsy can be severely impacted. Neuropsychiatric disorders such as depression and ADHD are also typically treated with medications that have deleterious side effects and lack of efficacy. To offer patients relief that medication alone cannot deliver, various neurostimulation methods have been developed. For example, vagus nerve stimulation (VNS) has been shown to be therapeutically useful. Similarly, deep brain stimulation (DBS) and responsive neurostimulation (RNS) approaches are known to have efficacy. But these neurostimulation techniques are invasive as they require surgical implantation of electrodes. Thus, these techniques are relatively expensive and involve the dangers associated with the surgical implantation of the electrodes.

To provide neurostimulation without the invasive dangers of prior art techniques, an alternative neurostimulation therapy has been developed that involves trigeminal nerve stimulation (TNS). For example, a cutaneous embodiment of TNS involves the transcutaneous stimulation of the supraorbital nerves and/or the supratrochlear nerves in the forehead. Like other cranial nerves, the supraorbital and supratrochlear nerves arise through foramina in the skull. The supraorbital nerve arises from the supraorbital foramen above the orbit. Since one has two eyes, there are thus two supraorbital nerves that ascend vertically toward the scalp from their respective foramen. The supratrochlear nerve is medial with regard to the supraorbital. But it also then ascends vertically towards the hairline. There are thus two supratrochlear nerves, each arising from its respective orbit. A supraorbital nerve and supratrochlear nerve thus associates with each orbit. The forehead is thus an ideal location to stimulate the trigeminal nerve in that the supraorbital nerve and supratrochlear nerve associated with each orbit are located medially on the forehead. The skin and fascia over the forehead is relatively thin such that the supratrochlear and supraorbital nerves are readily stimulated transcutaneously.

Although TNS has shown great promise, there remains a need in the art to tailor TNS to particular disorders.

BRIEF DESCRIPTION OF THE DRAWINGS

The present disclosure, both as to its organization and manner of operation, may be understood by reference to the following description, taken in connection with the accompanying drawings, in which.

DETAILED DESCRIPTION

In the least invasive form of TNS, a cutaneous electrode assembly is applied to the forehead to stimulate the ophthalmic nerves. The electrode assembly extends longitudinally from at least a first electrode contact and across a central insulating to at least a second electrode contact. Such a longitudinal extent is quite advantageous in that a lay person can readily center an electrode assembly on their forehead adjacent to or above their eyebrows. In some embodiments, the electrode assembly may include an alignment feature such as a centrally-located angular point that a lay person may also easily align with their nasal midline. The central insulating region is sized such that, with the electrode assembly centered on the forehead, the first electrode contact overlays the supratrochlear nerve and/or the supraorbital nerve arising from a first orbital arch and such that the second electrode contact overlays the supraorbital nerve and/or the supratrochlear nerve arising from a remaining second orbital arch. Thus, a lay person can position and apply the cutaneous electrode assembly so that the ophthalmic nerves are electrically stimulated by the corresponding electrode contacts without requiring any specialized training or anatomical knowledge. Moreover, because the ophthalmic nerves on the forehead are relatively shallow with regard to the skin surface, they are readily stimulated by cutaneous electrodes at current levels that are easily tolerated by patients. The amount of current may thus be regulated so that the brain itself is never subjected to any current (or subjected to vanishingly—small amounts of current that have no deleterious effects). A cutaneous electrode application to the forehead thus involves none of the risks involved with the conventional invasive approaches and also isolates the brain from exposure to electrical current.

Figure 1:
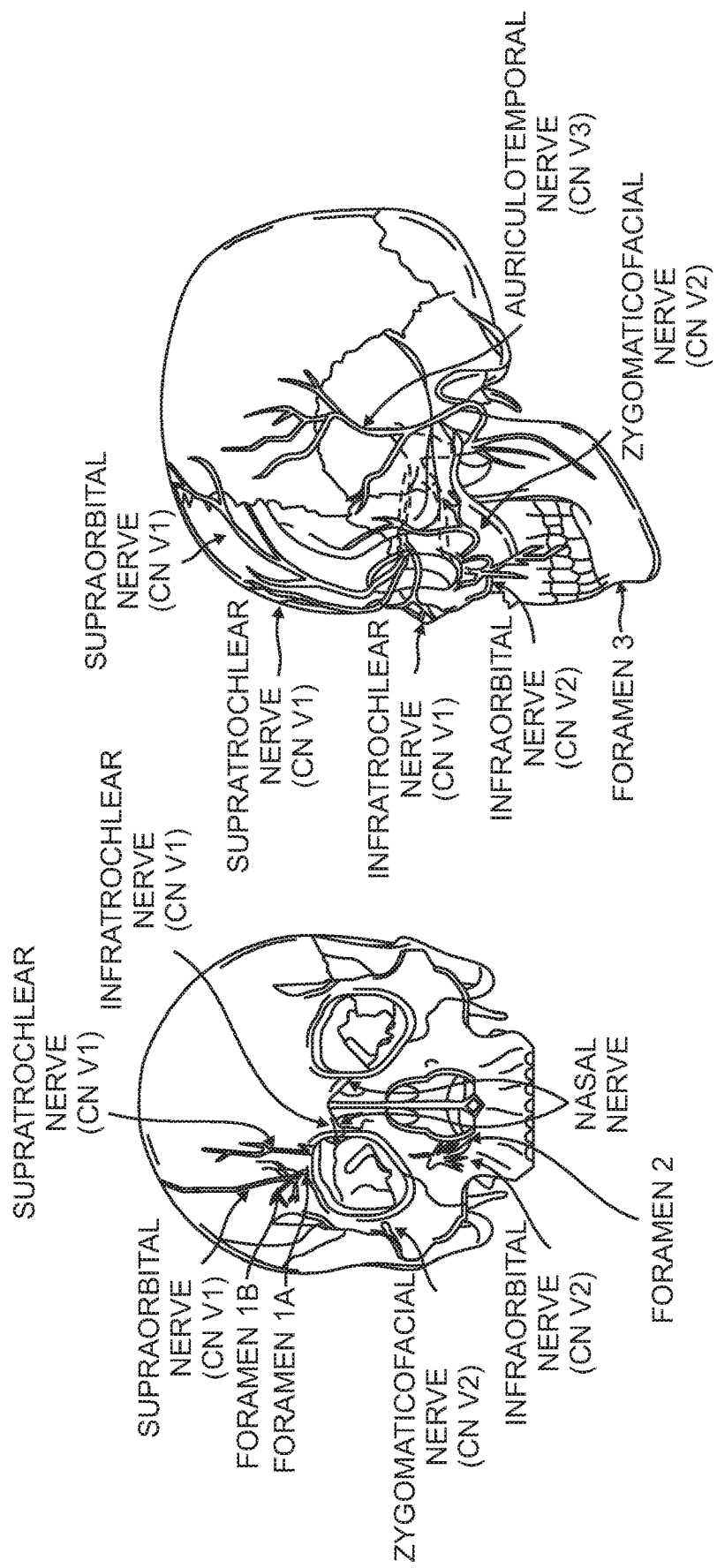
FIGS. 1A and 1B illustrate the location of several branches (nerves) of the trigeminal nerve and the location of the major foramina for the superficial branches of the trigeminal nerve.

The cutaneous electrode assembly may be applied for acute or prolonged treatment. In one embodiment, the electrode assembly may be applied for a limited period of time. The electrode assembly can then be removed so that a patient can resume their normal routine. To better appreciate the features of the TNS techniques discussed herein, a brief review of the trigeminal nerve and the subcutaneous and connective tissue of the human head that overlies the trigeminal nerve is now provided. With reference to FIGS. 1A and 1B, the trigeminal nerve is the largest cranial nerve and has extensive connections with the brainstem and other brain structures. The trigeminal nerve, also named the fifth cranial nerve or "CN V," has three major sensory branches over the face, all of which are bilateral, and highly accessible. The ophthalmic nerve is frequently referred to as the $V_1$ division and includes the supraorbital and supratrochlear nerves that supply sensory information about pain, temperature, and light touch to the skin of the forehead, the upper eyelid, the anterior part of the nose, and the eye. The $V_2$ division includes the infraorbital and maxillary nerves. The infraorbital branch supplies sensory information about pain, temperature, and light touch sensation to the lower eyelid, cheek, and upper lip. Finally, the $V_3$ division includes the auriculotemporal, lingual, and inferior alveolar branches of the mandibular nerves. The inferior alveolar branch supplies similar sensory modalities to the skin of the lower face (e.g. jaw and tongue) and lips. All three divisions supply sensory modalities to internal structures of the head such as the meninges.

These branches exit the skull through three groups of foramina or notches, as shown in FIGS. 1A and 1B. The supraorbital and supratrochlear nerves exit at foramina 1. In particular, the foramen (or notch) for the supratrochlear nerve is approximately 2.1-2.6 cm from the nasal midline (in adults), and is located immediately above the orbital ridge that is located below the eyebrow. The supratrochlear foramen is indicated as foramen 1B. In contrast, the foramen (or notch) for the supraorbital nerve is located more laterally from the nasal midline: e.g., approximately 3.2 cm from the nasal midline in adults. This foramen is indicated as foramen 1A. The infraorbital branch or maxillary nerve exits at foramen 2, approximately 2.4-3.0 cm from the nasal midline (in adults) and the mentalis nerve exits at foramen 3, approximately 2.0-2.3 cm from the nasal midline (in adults). Other sensory branches, including the zygomaticofacial, zygomaticoorbital, zygomaticotemporal, and auriculotemporal, arise from other foramina.

Fibers from the three major branches join together to form the trigeminal ganglion. From there, fibers ascend into the brainstem at the level of the pons to synapse with the main sensory nucleus of the pons, the mesencephalic nucleus of V, and the spinal nucleus and tract of V. Pain fibers descend in the spinal nucleus and tract of V, and then ascend to the ventral posterior medial nucleus (VPM) of the thalamus, and then project to the cerebral cortex. Light touch sensory fibers are large myelinated fibers, which ascend to the ventral posterior lateral (VPL) nucleus of the thalamus, and also project to the cerebral cortex. Afferent sensory fibers project from the trigeminal nuclei to the thalamus and the cerebral cortex.

Figure 2:
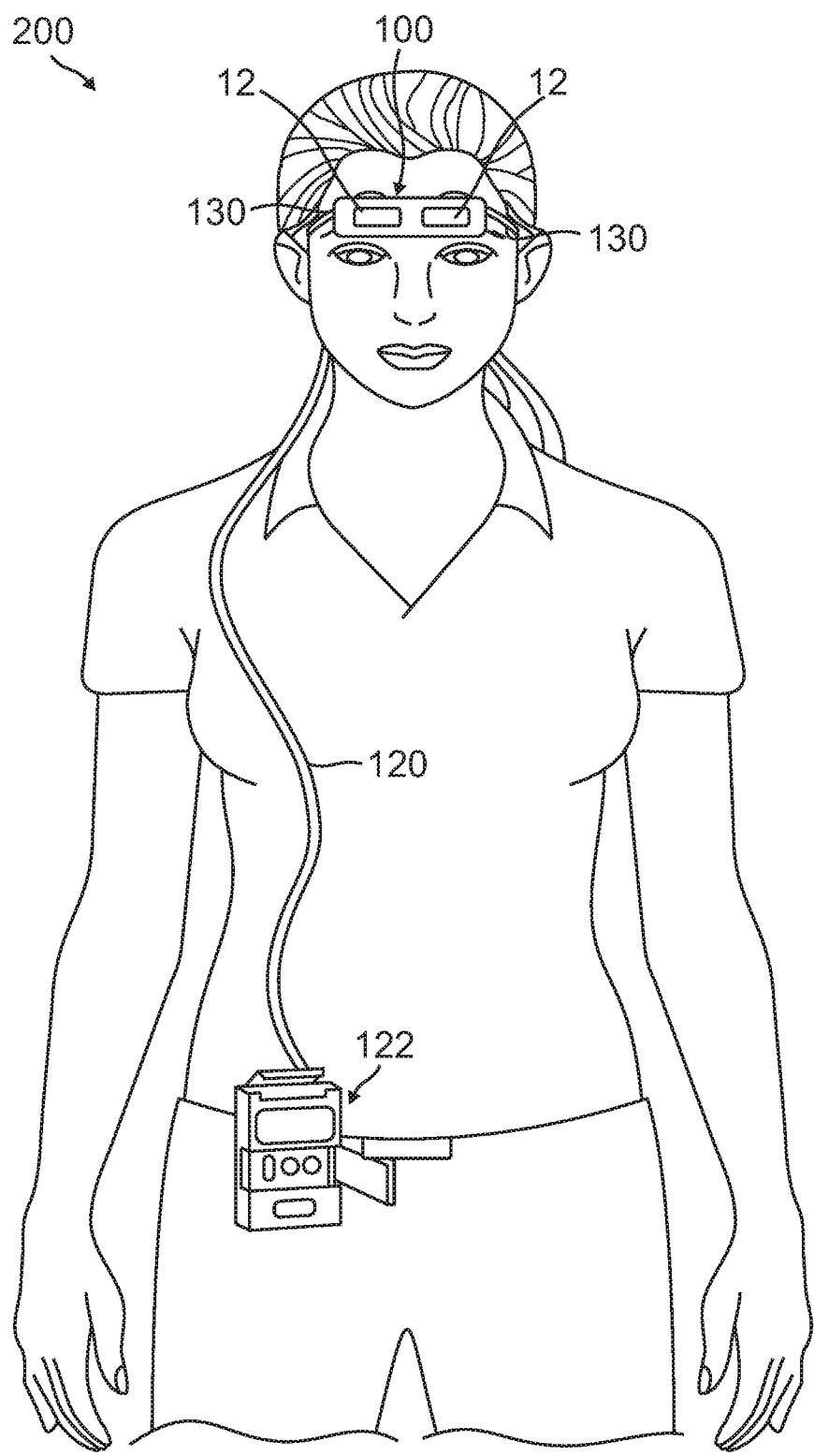
FIG. 2 depicts a patient with a cutaneous electrode system according to aspects of the present disclosure.

With regard to a given supraorbital arch (either the left or right side of the forehead), the corresponding supraorbital nerve and the adjacent supratrochlear nerve are referred to herein as an "ophthalmic nerve pair." In this fashion, the ambiguity that results from referring to just the supraorbital nerve (or the supratrochlear) as the "ophthalmic" nerve is avoided. Given the location of each ophthalmic nerve pair, they are readily stimulated by a cutaneous electrode assembly having electrode contacts 12 such as shown in FIG. 2 for a system 200 including a cutaneous electrode assembly 100, electrical cable or wire 120 and an external neurostimulator or pulse generator 122. In system 200, electrode assembly 100 includes a pair of electrode contacts 12 that are positioned for the bilateral simultaneous stimulation of both ophthalmic nerve pairs. Referring back to the nerve locations as discussed with regard to FIGS. 1A and 1B, note that there is an electrode contact 12 in system 200 over and lateral to each supraorbital nerve. A current driven through one electrode contact 12 will thus pass across not only the supraorbital nerves but also across the supratrochlear nerves. As shown in FIG. 1A, each supraorbital nerve arises from its foramen or notch 1A just medially to the center of each supraorbital ridge. Referring again to FIG. 2, cutaneous TNS excitation is thus readily achieved by lay people in that each electrode assembly 100 is readily centered on the forehead such that each electrode contact 12 is positioned over or adjacent to each supraorbital nerve foramen or notch so as to stimulate the corresponding ophthalmic nerve pair. The width of each electrode contact 12 may be such that it is greater than the expected spacing between the supraorbital nerve and the supratrochlear nerve in a given ophthalmic nerve pair. This is quite advantageous as compared to prior art TNS approaches in which individual contacts were positioned by palpating for the supraorbital notch or foramen and attaching an electrode over or above the foramen. Such an individual contact placement is problematic in that a lay person may not attach the contacts properly, which may result in excessive current exposure such that the brain itself receives appreciable currents. For example, currents tend to penetrate deeper as the electrode spacing is increased. A lay person could thus space individually-placed electrodes too far apart so as to raise the danger of exciting deeper currents that penetrate to the brain. But with electrode assembly 100, the lay person may readily center its midline with the nasal midline. Since the electrode contacts 12 are positioned apart so that each electrode contact 12 stimulates the underlying ophthalmic nerve pair when electrode assembly 100 is centered with regard to the nasal midline, the problems and dangers of prior art individual electrode application are avoided.

The pulse generator 122 is portable and attached to, for example, a belt of the patient. However, either a portable or non-portable pulse generator may be used. In alternative embodiments discussed further below, electrode assembly 100 may be integrated with a pulse generator. In some embodiments, the system 200 may also include a regulation device (not illustrated) to ensure safe use of the system. The regulation device is configured to be attached to or integrated with the pulse generator 122 and is configured to govern the maximum charge balanced output current below approximately 10-20 mA to minimize current penetration to the brain and increase patient tolerance. The regulation device may be internally programmed to range from 0.25-5.0 mA, 0-10 mA, 0-15 mA, depending on the surface area, placement, and orientation of the electrode assembly 100, and whether the electrode assembly 100 is stimulating near or adjacent to the skull, or away from the skull, where current ranges may be higher or lower. In contrast, conventional TENS units stimulate with maximum output currents of up to 100 mA, which result in currents which may penetrate the skull and which may not be well tolerated.

In some embodiments, the electrode assembly 100 further includes a retainer element 130 configured to secure the electrode assembly to a patient's forehead. In one embodiment, the retainer element 130 can be an elastic band or strap that encircles the back of the head to secure electrode assembly 100 to the patient. In alternative embodiments, the electrode assembly 100 can be secured in place by a hat or a cap which also serves to conceal the electrode assembly 100 from view. In still other embodiments, the electrode assembly 100 may be secured by adhesive, such as an adhesive strip, an adhesive backing surrounding the conducting area or an adhesive conductive gel.

Figure 3A:
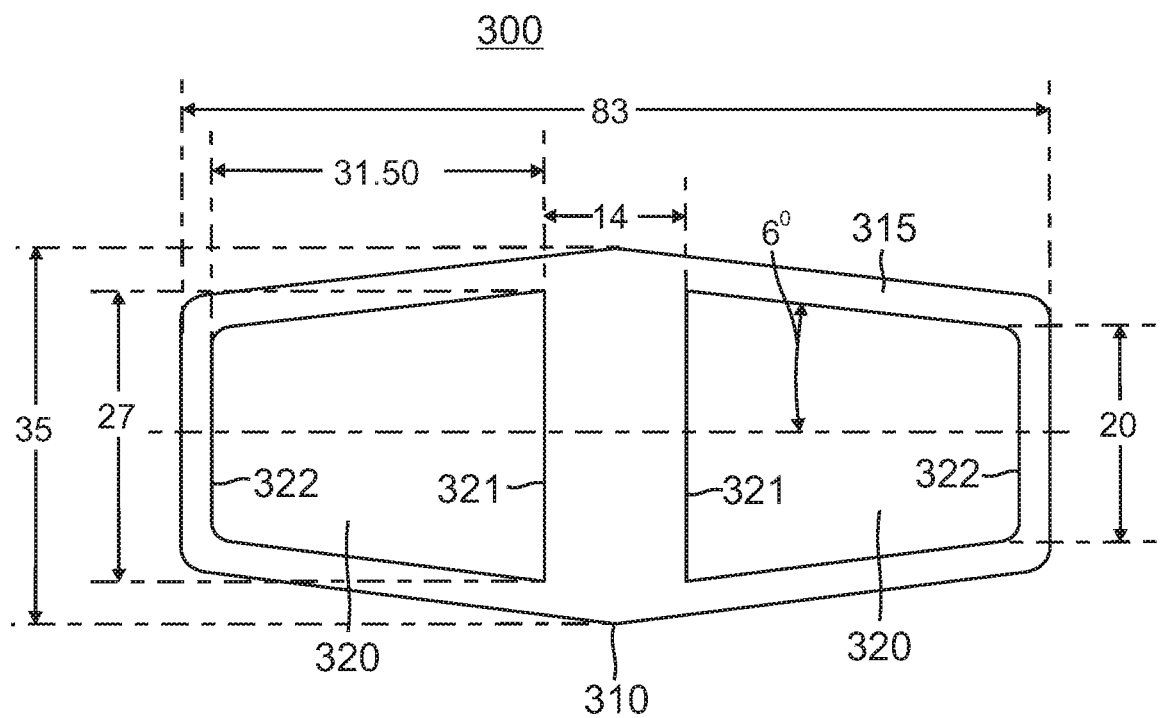
FIG. 3A is a plan view of a cutaneous electrode assembly that includes a pair of contacts configured to stimulate both ophthalmic nerve pairs.

Referring now to FIG. 3A, an example electrode assembly 300 includes a pair of electrode contacts 320 received in apertures within an adhesive-covered foam layer 315. For example, foam layer 315 may comprise a medical grade foam layer and electrode contacts 320 may comprise a conductive hydrogel electrically driven by an electrode pad (not illustrated). To assist in the alignment of electrode assembly 300 with the nasal midline, a midline alignment feature such as a convex angle 310 (e.g., an angle of 168 degrees) may be defined by the bottom and top edges of foam layer 315. Alternatively, only one of the bottom or top edges of foam layer 315 may include such an alignment feature. Gel pads 320 are separated by a central insulating region that may be 14 mm wide. Given the chevron shaping resulting from convex angles 310, each electrode contact/gel pad 320 narrows by 12 degrees from a medial edge 321 that may be 27 mm wide to a lateral edge 322 that may be 20 mm wide. Each gel pad 320 may have a longitudinal extent of 31.5 mm. The lateral edge 322 of each gel pad 320 is thus 38.5 mm from the nasal midline. Such a pad spacing assures that each gel pad 320 is positioned to stimulate both the supraorbital nerve and the supraorbital nerve in an ophthalmic nerve pair for the vast bulk of the adult population. But some adults will require even a greater pad width such as 34 mm to assure that the supraorbital nerves receive adequate stimulation.

Figure 3B:
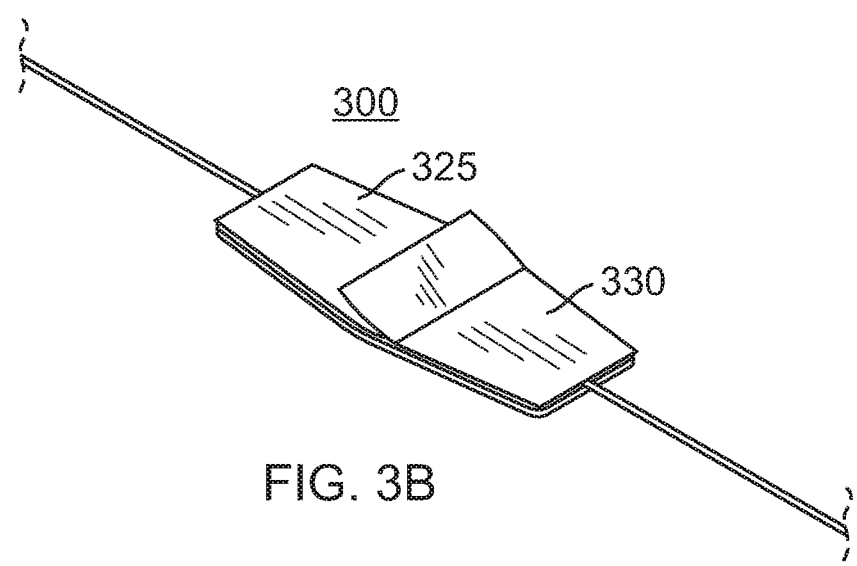
FIG. 3B is a perspective view of the cutaneous electrode assembly of FIG. 3A.

An additional foam layer (not illustrated) serves as a back wall to the apertures in foam layer 315 that receive gel pads 320. Prior to application, gel pads 320 and the adhesive surface of foam layer 315 are protected by, for example, by waxed paper flaps 330 and 325 as shown in FIG. 3B. Flaps 330 and 325 function in the familiar "band aid" fashion such that each flap includes a projecting end that a user may readily pull on to release the corresponding flap from windowed electrode assembly 300. With the gel pads 320 and the adhesive surface then uncovered, the patient may proceed to adhere electrode assembly 300 to their forehead as discussed with regard to FIG. 2.

Regardless of whether a single pair of contacts are used to stimulate both ophthalmic nerve pairs or whether each ophthalmic nerve pair is stimulated by its own pair of contacts, the current may be pulsed at a stimulus frequency between about 2 Hz and about 500 Hz (e.g., at a frequency of between 2 Hz and 100 Hz, at a frequency of between 20 Hz and 300 Hz, at a frequency of between 100 Hz and 500 Hz, etc.), at a pulse duration between 50 microseconds (μsec) and 250 μsec, at an output current density of less than 25 mA/cm2 and an output charge density of less than 10 μCoulomb/cm2 at the cerebral cortex for at least one-half to one hour per day. The pulsing may be performed in a duty cycle of 30 seconds of pulsing following by 30 seconds of rest.

In various embodiments, the stimulation is delivered at a specific pulse width or range of pulse widths (or pulse duration). The stimulation can be set to deliver pulse widths in any range within a lower limit of about 10 microseconds and an upper limit of about 3 seconds. In various embodiments, the stimulation can be set to deliver pulse widths in the range greater than and/or less than one or more of 50 μs, 60 μs, 70 μs, 80 μs, 90 μs, 100 μs, 125 μs, 150 μs, 175 μs, 200 μs, 225 μs, 250 μs, up to 500 μs. Those of skill in the art will recognized that one or more of the above times can be used as a border of a range of pulse widths.

In some embodiments, the stimulation amplitude is delivered as a voltage or current controlled stimulation. In other embodiments it can be delivered as a capacitive discharge. In various embodiments, the current amplitude can be in any range within a lower limit of about 300 μA and an upper limit of about 30 mA-35 mA, depending on the surface area of the electrodes, inter-electrode distance, the branch(es) stimulated, and the modeling data as described above. In various embodiments, the amplitude can be in a range greater than and/or less than one or more of 50 μA, 75 μA, 100 μA, 125 μA, 150 μA, 175 μA, 200 μA, 225 μA, 250 μA, 275 μA, 300 μA, 325 μA, 350 μA, 375 μA, 400 μA, 425 μA, 450 μA, 475 μA, 500 μA, 525 μA, 550 μA, 575 μA, 600 μA, 625 μA, 650 μA, 675 μA, 700 μA, 725 μA, 850 μA, 875 μA, 900 μA, 925 μA, 950 μA, 975 μA, 1 mA, 2 mA, 3 mA, 4 mA, 5 mA, 6 mA, 7 mA, 8 mA, 9 mA, 10 mA, 11 mA, 12 mA, 13 mA, 14 mA, 15 mA, 16 mA, 17 mA, 18 mA, 19 mA and 20 mA. Those of skill in the art will recognize that one or more of the above amplitudes can be used as a border of a range of amplitudes.

In various embodiments, the stimulation can be delivered at one or more frequencies, or within a range of frequencies. The stimulation can be set to be delivered at frequencies in any range within an upper limit of about 500 Hz and a lower limit of about 2 Hz. In various embodiments, the stimulation can be set to be delivered at frequencies less than, and/or greater than one or more of 50 Hz, 45 Hz, 40 Hz, 35 Hz, 30 Hz, 25 Hz, 20 Hz, 15 Hz, or 10 Hz. In various embodiments, the stimulation can be set to be delivered at frequencies greater than, and/or less than, one or more of 20 Hz, 30 Hz, 40 Hz, 50 Hz, 60 Hz, 70 Hz, 80 Hz, 90 Hz, 100 Hz, 125 Hz, 150 Hz, up to 300 Hz. Those of skill in the art will recognize that one or more of the above frequencies can be used as a border of a range of frequencies.

In various embodiments, the stimulation is delivered at a specific duty cycle or range of duty cycles within a range from 100% down to about 5%. The duty cycle is defined with regard to a duty cycle period. In each duty cycle period, the current is pulsed during an on portion of the duty cycle period and not pulsed during a remaining off portion of each duty cycle period. The ratio of the on portion to the duty cycle period defines the duty cycle. For example, if the on portion is one half of the duty cycle period, the duty cycle would be 50%. In various embodiments, the stimulation can be set to be delivered at a duty cycle in the range greater than and/or less than one or more of 5%, 10%, 15%, 20%, 25%, 30%, 35%, 40%, 45%, 50%, 55%, 60%, 65%, 70%, 75%, 80%, 85%, 90%, 95%, or 100%. The period used to define the duty cycle may be 60 seconds such that a 50% duty cycle would comprise 30 seconds of pulsing and 30 seconds of quiescence in each duty cycle period. In some embodiments, to ensure preservation of the nerve, a duty cycle of 10% to 50% may be preferable. In some embodiments, duty cycles up to 100% may be useful in particular circumstances. Those of skill in the art will recognize that one or more of the above percentages can be used as a border of a range of duty cycles.

Applicant has discovered that pulse repetition frequency may be dispositive for certain disorders whereas it is the number of pulses that is more important for other disorders. For example, the efficacy of the TNS anti-epileptic effect is maximized at frequencies of approximately 100 Hz or greater. Animal studies have shown that this is likely related to the maximum rate of firing for neurons involved in the trigeminal system, and that once the stimulation exceeds a certain threshold neurons are kept in their refractory state, which keeps them at a low-level of activity that inhibits the propagation and spread of seizures.

In addition to epilepsy, TNS has been studied as a therapy for major depressive disorder (MDD) and other neuropsychiatric disorders. Human neuroimaging studies of subjects with MDD have demonstrated that TNS increases regional activity in areas of the brain known to be hypoactive in subjects with depression and other neuropsychiatric disorders. Thus it seems likely that the mechanism of action for the anti-depressive effect of TNS is substantially different than the mechanism of the anti-epileptic effect. Whereas in epilepsy the goal is to decrease activity by stimulating neurons at a rate faster than they can effectively process, the goal in depression and other neuropsychiatric disorders is to increase activity in brain regions functioning at an undesirably low level.

In that regard, Applicant has discovered that, surprisingly, it is the number of pulses delivered to the patient that matters with regard to the treatment of depression and other neuropsychiatric disorders. In other words, the number of pulses is more of a first-order effect whereas the pulse repetition frequency and pulse width are more second-order. In that regard, so long as a pulse has a sufficient pulse width of, for example, 50 microseconds or greater, the resulting TNS therapy can be provided on a pulse number basis. This is quite advantageous in that a relatively low pulse frequency may be better tolerated by a patient. For example, a pulse rate of just 2 Hz may be used. The amount of time for TNS therapy is then a function of the pulse rate and the duty cycle (such as 30 seconds on and 30 seconds off) that delivers the desired number of pulses. For example, studies have shown that daily administration of 1800 pulses is sufficient to provide measurable relief for depression.

Not only are the number of pulses dispositive but temporal considerations are also a factor. For example, the areas of the brain that are active vs. deactivated depend upon whether the patient is sleeping or awake and also upon the time of day for both states. The pattern and strength of functional connections between brain regions is different in these two brain states. The pattern of activation and the pattern and strength of connections among brain regions also are known to vary over the course of the day. The brain state is thus also influenced by the "circadian" or "diurnal" rhythm patterns, and under specific circumstances, these internal chronobiological patterns may or may not be in synchrony with the external environment (e.g., daily patterns of day and night) depending upon the disorder and upon external factors (e.g., after travel crossing time zones, related to shift-work).

Parameters for pulses to be administered to a patient may be determined based upon a disorder being treated. The parameters may include number of the pulses, a pulse repetition frequency, or both. The parameters may further include a pulse width, pulse duration, and/or a duty cycle for the pulses.

A disorder to be treated may be associated with an undesirably high activity in a target brain region or an undesirably low activity in a target brain region. The parameters may be determined based on whether the disorder of the patient is associated with an undesirably high activity in a target brain region or an undesirably low activity in the target brain region. Alternatively, or additionally, whether it is the number of the pulses that is determined or the pulse repetition frequency that is determined may be based on whether the disorder is associated with an undesirably low activity in a target brain region or an undesirably high activity in a target brain region. In an example, the determination that a disorder is associated with an undesirably low activity or an undesirably high activity at a target brain region may be made based on the pathology of the patient's disorder. In another example, the determination that a disorder is associated with an undesirably low activity or an undesirably high activity at a target brain region may be made based on a medical diagnosis of the patient's disorder (e.g., by a clinician). Clinicians such as medical doctors may recognize that a certain disease is associated with an undesirably high or low activity in a brain region. In a further example, the determination that a disorder is associated with an undesirably low activity or an undesirably high activity at a target brain region may be made based on a brain scan of the patient's brain.

In an example, a number of the pulses to be administered to a patient is determined based on a disorder being treated. The determination of the number of pulses may be in response to determining that the disorder is associated with an undesirably low activity in a target brain region. The disorder may be a mood disorder, a cognitive disorder, a pain disorder, a behavioral disorder, a movement disorder, a disorder due to a brain injury or a traumatic experience, or other disorder that may be associated with an undesirably low activity in a target brain region. The pulses may then be administered to increase activity in the target brain region.

In another example, a pulse repetition frequency of the pulses to be administered to a patient is determined based on a disorder being treated. The determination of the pulse repetition frequency may be in response to determining that the disorder is associated with an undesirably high activity in a target brain region. The disorder may be a seizure disorder such as epilepsy, a pain disorder, a movement disorder, a behavioral disorder, a mood disorder, a disorder due to a brain injury or a traumatic experience, or other disorder that may be associated with an undesirably high activity in a target brain region. The pulses may then be administered to lower activity in the target brain region.

A pulse generator such as pulse generator 122 shown in FIG. 2 may be configured to determine a number of pulses to be administered to the patient based upon a disease to be treated, pulse current through the electrode assembly to stimulate the patient's supraorbital and supratrochlear nerves, and track a number of administered pulses by counting the number of administered pulses or measuring an amount of time, wherein the pulsation of the current is stopped when the number of administered pulses reaches the determined number of pulses. In an example, pulse generator 122 may further determine whether the pulses are to be administered while the patient is awake, asleep, or both, determine whether the patient is awake or asleep, and pulse the current based on whether the patient is awake or asleep. In another example, pulse generator 122 may determine whether the pulses are to be administered at a particular time of day, in relationship to the intrinsic rhythms of the patient, based upon the disorder being treated, determine a time of day, and pulse the current based on the time of day.

Pulse generator 122 may determine parameters for pulses to be administered to a patient based upon a disorder being treated. For example, the pulse generator 122 may receive the parameters for the pulses from a clinician who determines the parameters for the pulses based on the disorder. In another example, an association between disorders and parameters may be preprogrammed such that a disorder may be selected by a user and, in response, pulse generator 122 determines the parameters for the pulses based on the disorder. Multiple parameters may be stored in a memory or other storage device that is coupled to, or a part of, pulse generator 122. A plurality of disorders may each be associated with one or more parameters. A disorder with an undesirably low activity in a brain region may be associated with parameters such as a pulse repetition frequency that is above a threshold for increasing activity in the brain region and below a threshold for synaptic fatigue of the neurons of the supraorbital and supratrochlear nerves (e.g., a pulse repetition frequency of between 2 Hz and 100 Hz). A disorder with an undesirably high activity in a brain region may be associated with parameters such as a pulse repetition frequency that exceeds a threshold for synaptic fatigue of the neurons of the supraorbital and supratrochlear nerves (e.g., a pulse repetition frequency of between 100 Hz and 500 Hz). Each disorder may have more than one set of parameters associated with it such that more than one options is given for a selected disorder.

The neurostimulation of the ophthalmic nerve pairs is not limited to cutaneous embodiments. In other embodiments, the electrode assembly may be a subcutaneous electrode assembly such as discussed in U.S. application Ser. No. 12/898,696, the contents of which are incorporated by reference herein.

The above specification, examples and data provide a complete description of the structure and use of exemplary embodiments of the invention as claimed below. Although various embodiments of the invention as claimed have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A method, comprising:
    determining a number of pulses to be administered to a patient based upon a disorder being treated;
    pulsing current through an electrode assembly to stimulate supraorbital and supratrochlear nerves on the patient with the determined number of pulses; and
    tracking a number of administered pulses by counting the number of administered pulses or measuring an amount of time, wherein the pulsation of the current is stopped when the number of administered pulses reaches the determined number of pulses.

2. The method of claim 1, further comprising:
    determining whether the pulses should be administered with the patient awake or asleep based upon the disorder being treated; and
    administering the pulses to the patient accordingly.

3. The method of claim 1, further comprising:
    determining whether the pulses should be administered at a particular time of day, in relationship to the intrinsic rhythms of the patient, based upon the disorder begin treated; and
    administering the pulses to the patient accordingly.

4. The method of claim 1, wherein the determining of the number of pulses is based on determining that the disorder is associated with an undesirably low activity in a brain region.

5. The method of claim 4, wherein the disorder is a mood disorder, a cognitive disorder, a pain disorder, a behavioral disorder, a movement disorder, or a disorder due to a brain injury or a traumatic experience.

6. The method of claim 4, wherein the pulsing is at a pulse repetition frequency that is above a threshold for increasing activity in the brain region and below a threshold for synaptic fatigue of the neurons of the supraorbital and supratrochlear nerves.

7. The method of claim 6, wherein the pulse repetition frequency is below 100 Hz.

8. The method of claim 1, further comprising tracking a number of administered pulses during the pulsing by counting the number of administered pulses or measuring an amount of time, wherein the pulsing of the current is stopped when the number of administered pulses reaches the determined number of pulses.

9. The method of claim 1, wherein the electrode assembly is a cutaneous electrode assembly, the method further comprising applying the cutaneous electrode assembly to the patient's forehead by aligning a midline of the cutaneous electrode assembly with the patient's nasal midline, and adhering the aligned cutaneous electrode assembly to the patient's forehead such that a first electrode contact overlays a first ophthalmic nerve pair on a first side of the patient's forehead and such that a second electrode contact overlays a second ophthalmic nerve pair on an opposing side of the patient's forehead.

10. A method, comprising:
    determining a pulse repetition frequency for pulses to be administered to a patient based upon a disorder being treated;
    pulsing current through an electrode assembly to stimulate the patient's supraorbital and supratrochlear nerves at the pulse repetition frequency; and
    tracking a number of administered pulses by counting the number of administered pulses or measuring an amount of time, wherein the pulsation of the current is stopped when the number of administered pulses reaches the determined number of pulses.

11. The method of claim 10, further comprising:
    determining whether the pulses should be administered with the patient awake or asleep based upon the disorder being treated; and
    administering the pulses to the patient accordingly.

12. The method of claim 10, further comprising:
    determining whether the pulses should be administered at a particular time of day, in relationship to the intrinsic rhythms of the patient, based upon the disorder begin treated; and
    administering the pulses to the patient accordingly.

13. The method of claim 10, wherein the determining of the pulse repetition frequency is based on determining the disorder is associated with an undesirably high activity in a brain region.

14. The method of claim 13, wherein the disorder is a seizure disorder, a pain disorder, a movement disorder, a behavioral disorder, a mood disorder, or a disorder due to a brain injury or a traumatic experience.

15. The method of claim 10, wherein the pulse repetition frequency exceeds a threshold for synaptic fatigue of the neurons of the supraorbital and supratrochlear nerves.

16. The method of claim 15, wherein the pulse repetition frequency is between 100 Hz and 500 Hz.

17. The method of claim 10, wherein the electrode assembly is a cutaneous electrode assembly, the method further comprising applying the cutaneous electrode assembly to the patient's forehead by aligning a midline of the cutaneous electrode assembly with the patient's nasal midline, and adhering the aligned cutaneous electrode assembly to the patient's forehead such that a first electrode contact overlays a first ophthalmic nerve pair on a first side of the patient's forehead and such that a second electrode contact overlays a second ophthalmic nerve pair on an opposing side of the patient's forehead.

18. A system comprising:
    an electrode assembly; and
    a pulse generator communicatively coupled to the electrode assembly, the pulse generator configured to:
        determine a number of pulses to be administered to the patient based upon a disease to be treated;

pulse current through the electrode assembly to stimulate the patient's supraorbital and supratrochlear nerves; and track a number of administered pulses by counting the number of administered pulses or measuring an amount of time, wherein the pulsation of the current is stopped when the number of administered pulses reaches the determined number of pulses.

19. The system of claim 18, wherein the pulse generator is configured to:

determine whether the pulses are to be administered while the patient is awake, asleep, or both;

determine whether the patient is awake or asleep; and pulse the current based on whether the patient is awake or asleep.

20. The system of claim 18, wherein the pulse generator is configured to:

determine whether the pulses are to be administered at a particular time of day, in relationship to the intrinsic rhythms of the patient, based upon the disorder begin treated;

determine a time of day; and pulse the current based on the time of day.

\* \* \* \* \*